US00PP35665P2

(12) United States Plant Patent
Mowrey et al.

(10) Patent No.: US PP35,665 P2
(45) Date of Patent: Feb. 27, 2024

(54) BLUEBERRY PLANT NAMED 'DRISBLUETWENTYNINE'

(50) Latin Name: ***Vaccinium corymbosum* L.**
Varietal Denomination: DrisBlueTwentyNine

(71) Applicant: Driscoll's, Inc., Watsonville, CA (US)

(72) Inventors: Bruce D. Mowrey, Watsonville, CA (US); Esther J. Kibbe, Watsonville, CA (US); Marta C. Baptista, Watsonville, CA (US); Raymond L. Jacobs, III, Watsonville, CA (US); Aleyna De La Luz Monroy, Watsonville, CA (US); James Olmstead, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 18/084,331

(22) Filed: Dec. 19, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP15,146 | P3 | 9/2004 | Hancock |
| PP19,503 | P3 | 11/2008 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Lyrene et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Rodriguez et al. |
| PP26,537 | P3 | 3/2016 | Caster et al. |
| PP26,643 | P3 | 4/2016 | Caster et al. |
| PP26,748 | P3 | 5/2016 | Rodriguez et al. |
| PP27,622 | P3 | 1/2017 | Caster et al. |
| PP28,933 | P2 | 2/2018 | Caster et al. |
| PP31,649 | P2 | 4/2020 | Caster et al. |
| PP31,650 | P2 | 4/2020 | Caster et al. |
| PP31,685 | P2 | 4/2020 | Mowrey et al. |
| PP31,698 | P2 | 4/2020 | Mowrey et al. |
| PP32,267 | P2 | 10/2020 | Caster et al. |
| PP32,744 | P3 | 1/2021 | Caster et al. |
| PP32,876 | P2 | 3/2021 | Mowrey et al. |
| PP33,066 | P2 | 5/2021 | Mowrey et al. |
| PP33,718 | P2 | 12/2021 | Caster et al. |
| PP34,067 | P2 | 3/2022 | Caster et al. |
| PP34,179 | P2 | 5/2022 | Mowrey et al. |
| PP34,316 | P2 | 6/2022 | Mowrey et al. |

*Primary Examiner* — Karen M Redden

(74) *Attorney, Agent, or Firm* — Morrison & Foerster LLP

(57) ABSTRACT

A new and distinct variety of blueberry plant named 'DrisBlueTwentyNine', particularly selected as an early to mid-season evergreen blueberry variety that has no chilling hours requirement to produce mid volumes of fruit in soil, as well as for the size and flavor of the fruit, is disclosed.

8 Drawing Sheets

Latin name: Botanical classification: *Vaccinium corymbosum* L.

Varietal denomination: The varietal denomination of the claimed variety of blueberry plant is 'DrisBlueTwentyNine'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum,* the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant ( *Vaccinium corymbosum* L.), which has been denominated as 'DrisBlueTwentyNine'.

Blueberry plant variety 'DrisBlueTwentyNine' was selected in Hillsborough County, Fla. in April of 2013 and originated from a controlled cross between the proprietary female parent blueberry plant '196H3' (unpatented) and the proprietary male parent blueberry plant '9J301' (unpatented). The original seedling of the new variety was first asexually propagated via. softwood cuttings and tissue culture in Santa Cruz County, Calif. in July of 2013.

'DrisBlueTwentyNine' was subsequently asexually propagated via softwood cuttings and tissue culture and underwent further testing in Ciudad Guzmán, Jalisco, México for four years (2015 to 2019). The present blueberry variety has been found to be stable and reproduce true to type through successive asexual propagations via softwood cuttings and tissue culture.

'DrisBlueTwentyNine' was selected as an early to mid-season evergreen blueberry variety that has no chilling hours requirement to produce mid volumes of fruit in soil, as well as for the size and flavor of the fruit.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are four years old, unless otherwise specified.

DETAILED BOTANICAL DESCRIPTION

Figure 1:
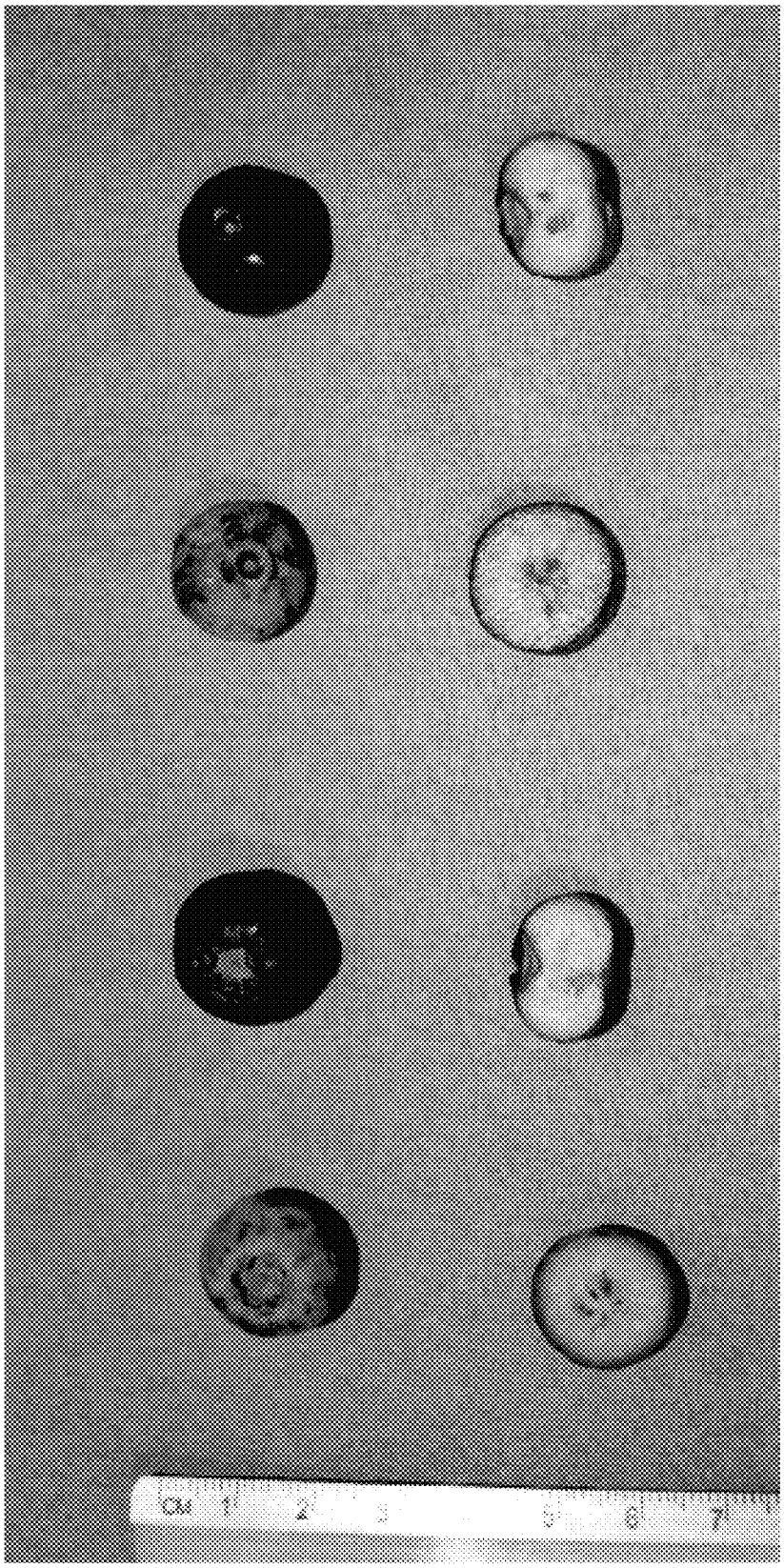
FIG. 1 illustrates whole fruit (left column, from top to bottom: pedicel side up, bloom removed; pedicel side up, bloom present; calyx side up, bloom removed; calyx side up, bloom present) and cross sections (right column, alternating between longitudinal and transverse sections) of variety 'DrisBlueTwentyNine'.
Figure 2:
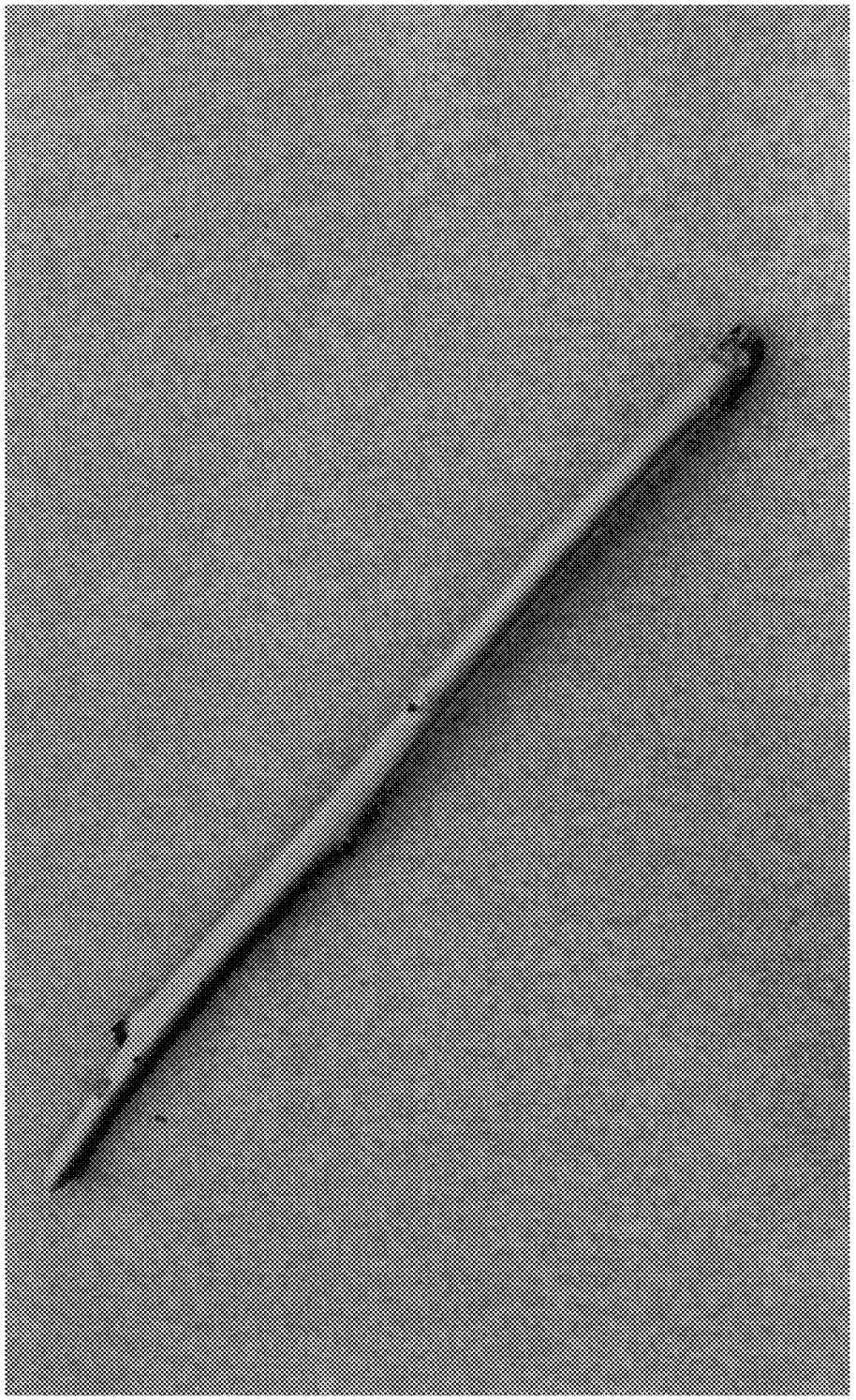
FIG. 2 illustrates a section of a cane of variety 'DrisBlueTwentyNine'.
Figure 3:
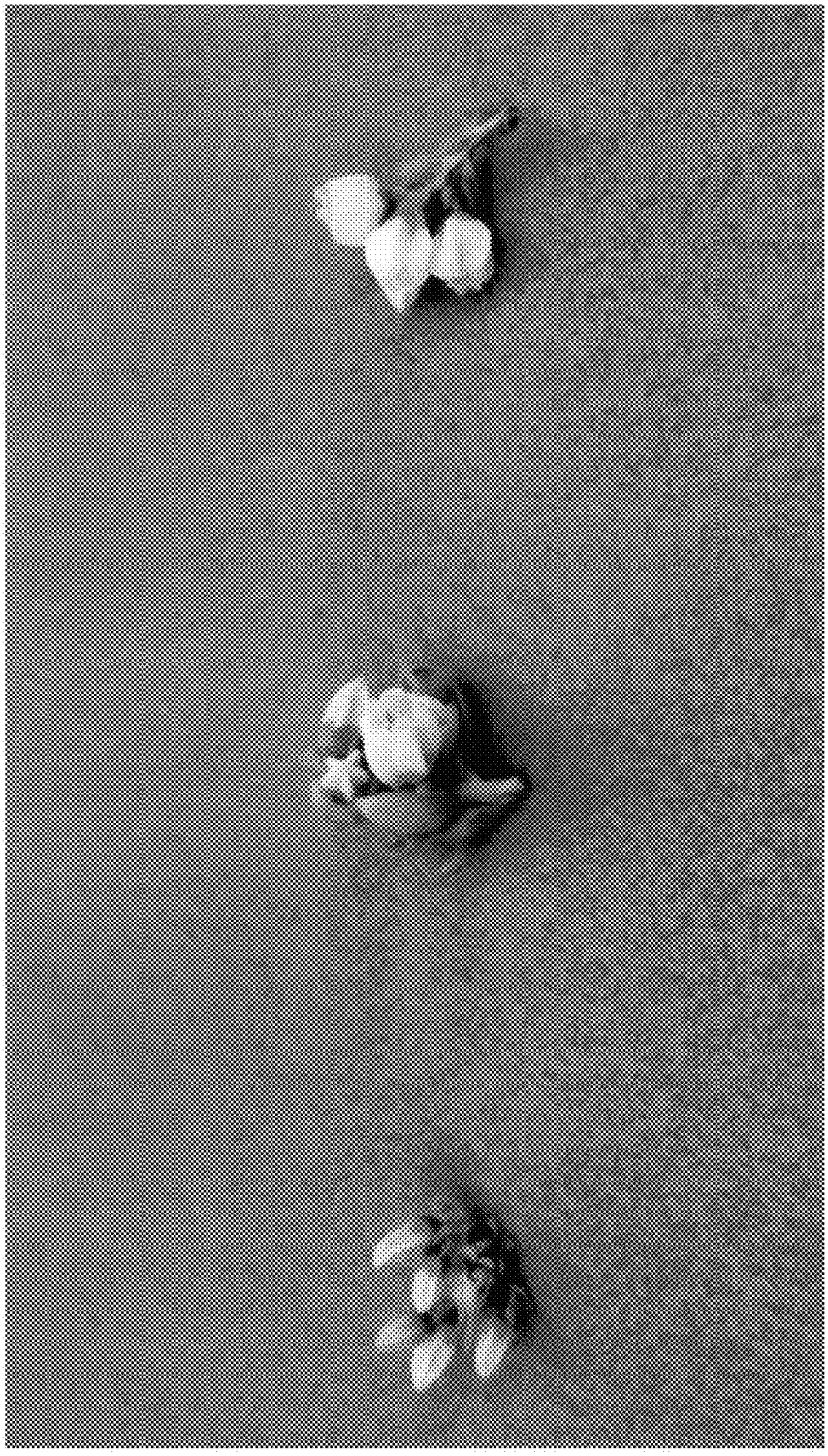
FIG. 3 illustrates clusters of flowers of variety 'DrisBlueTwentyNine'.
Figure 4:
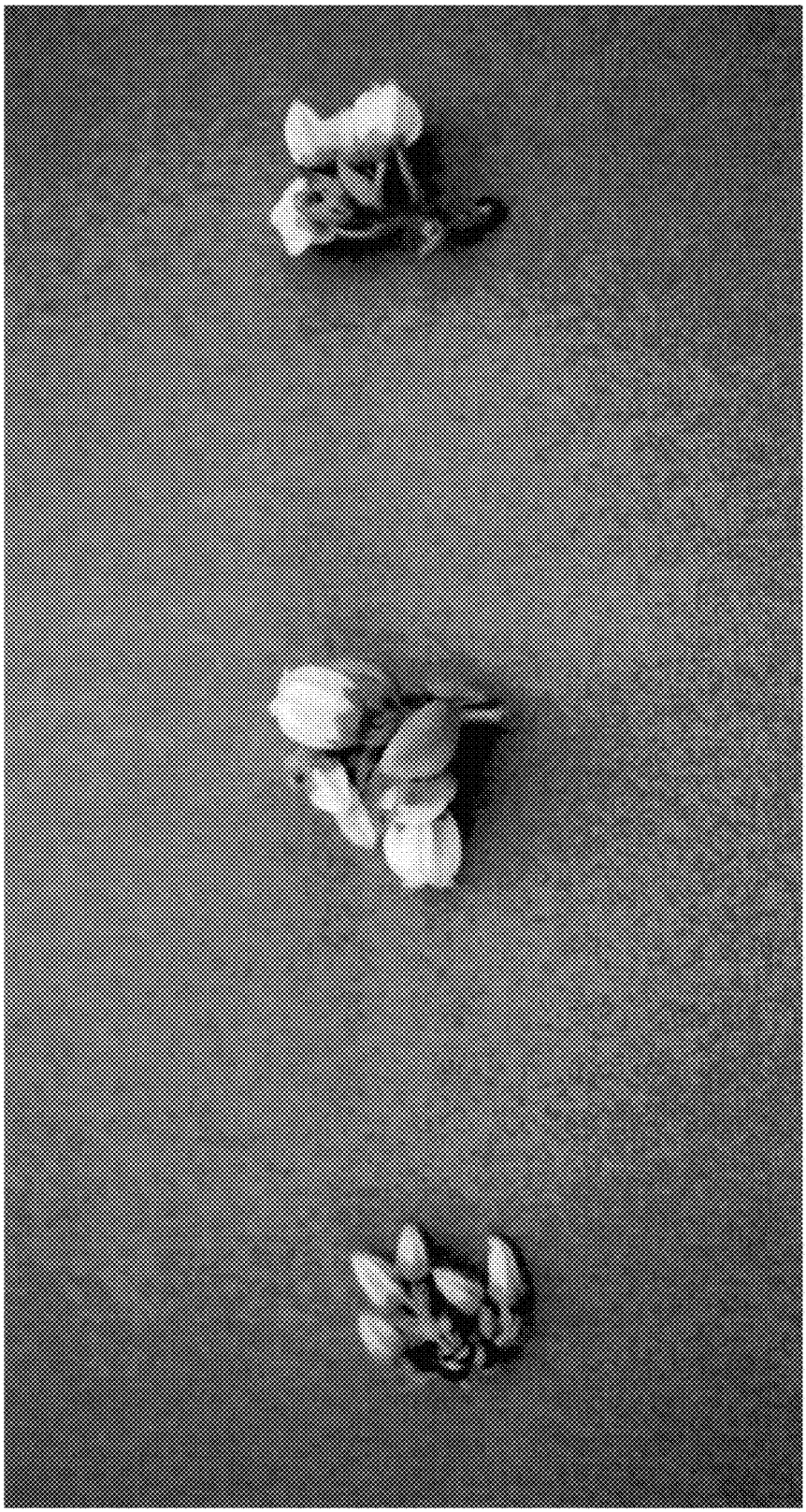
FIG. 4 illustrates another view of clusters of flowers of variety 'DrisBlueTwentyNine'.
Figure 5:
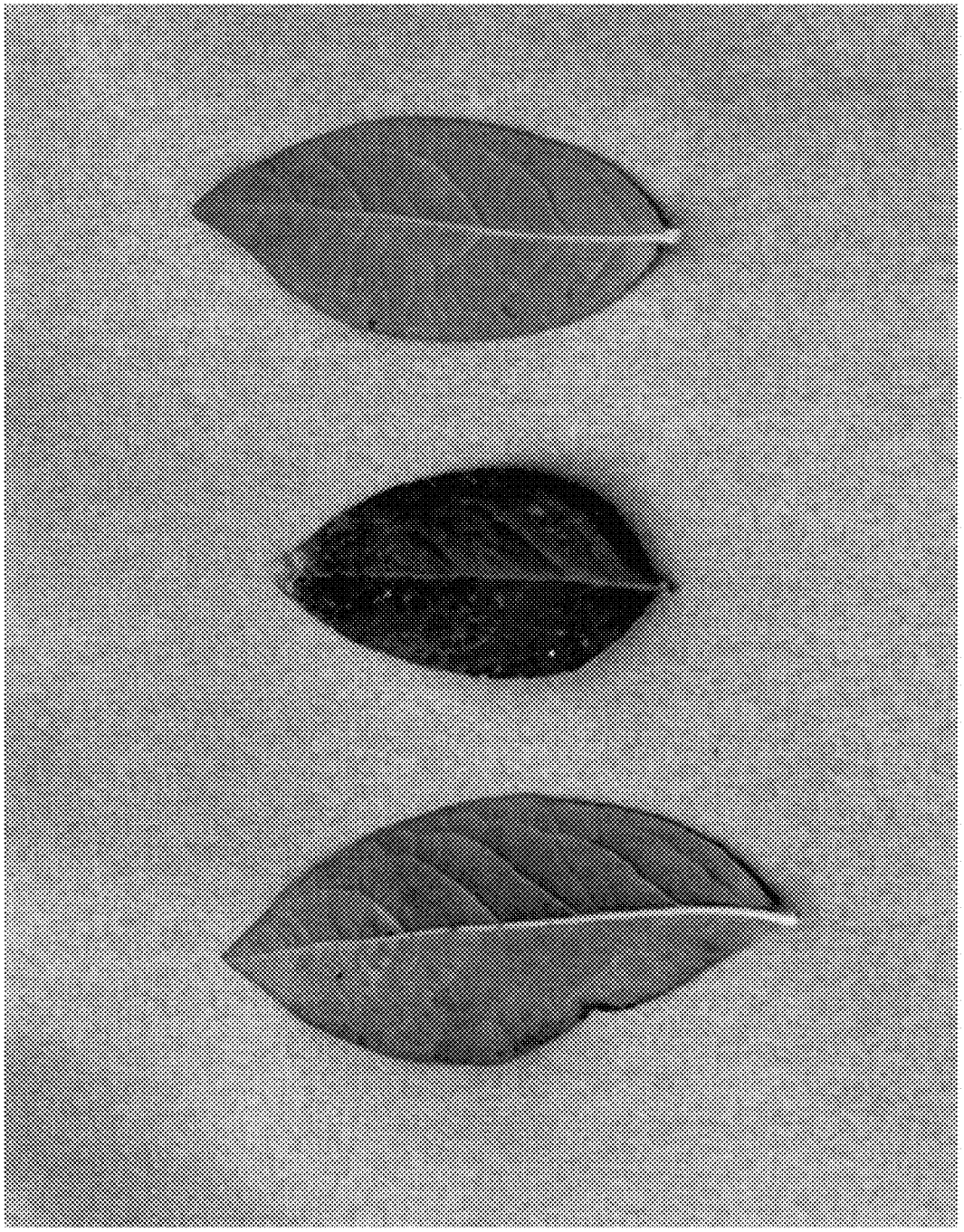
FIG. 5 illustrates the lower surface (left and right) and upper surface (middle) of leaves of variety 'DrisBlueTwentyNine'.
Figure 6:
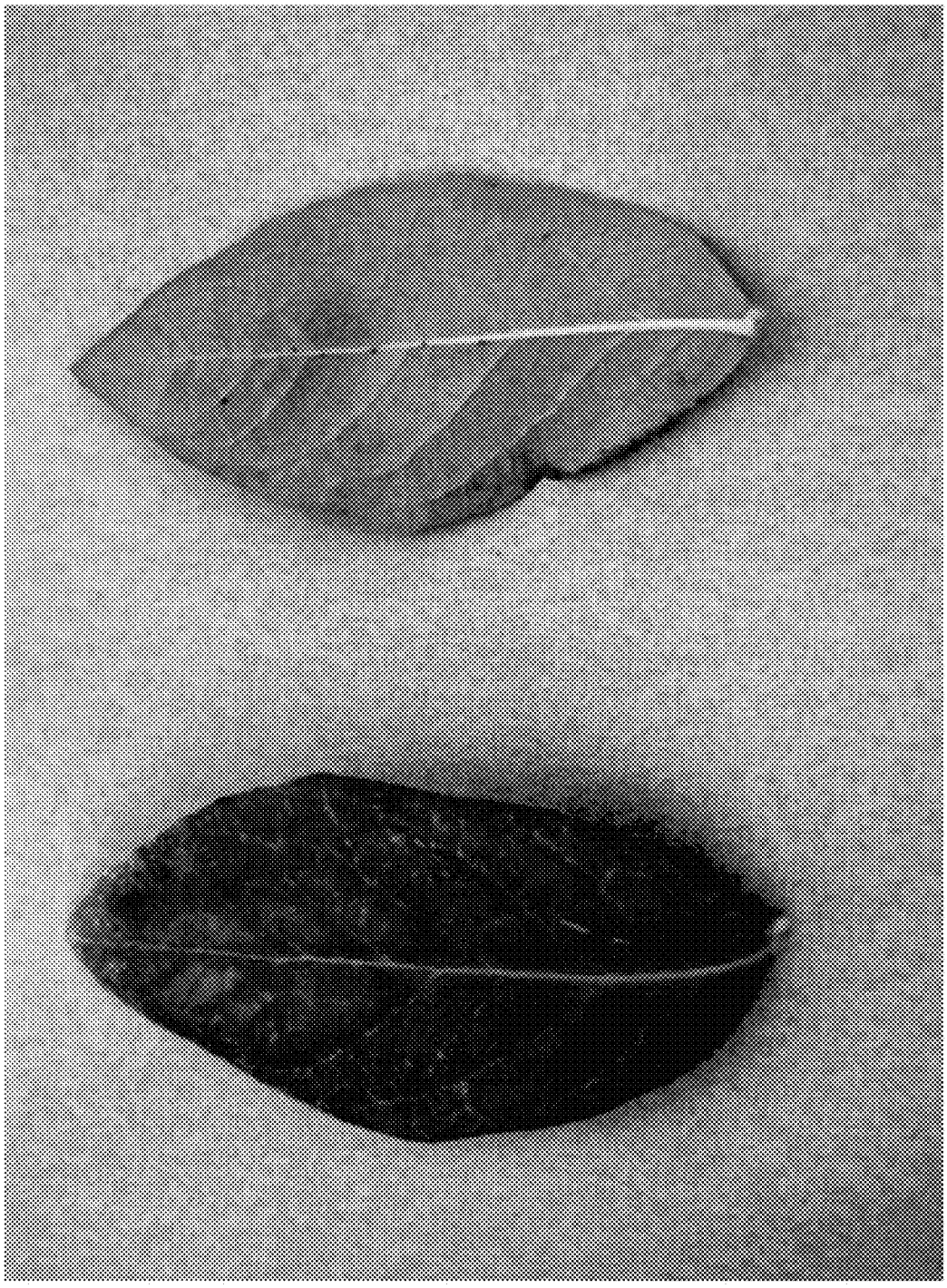
FIG. 6 illustrates another view of the upper surface (left) and lower surface (right) of leaves of variety 'DrisBlueTwentyNine'.
Figure 7:
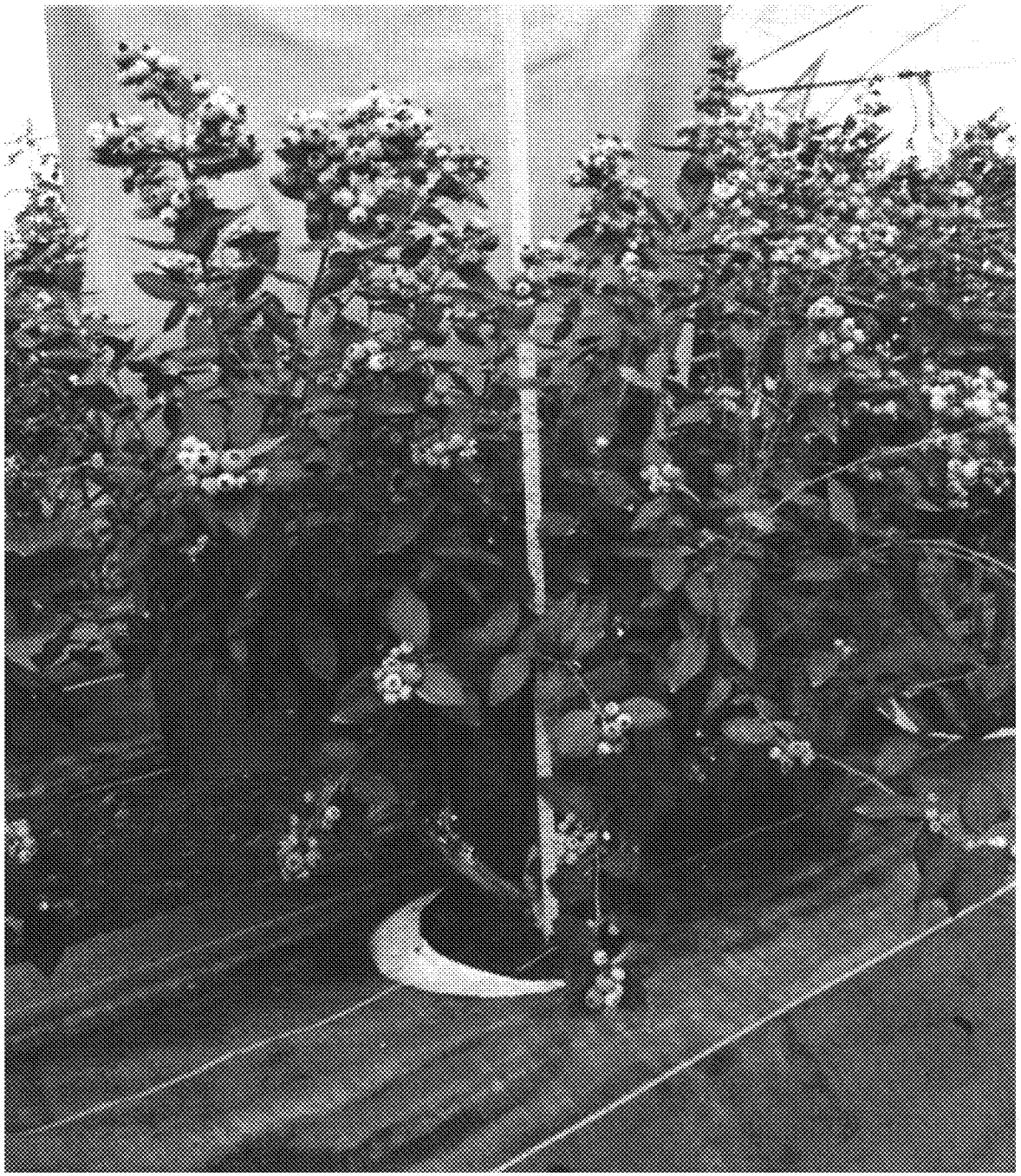
FIG. 7 illustrates a whole plant of variety 'DrisBlueTwentyNine'.
Figure 8:
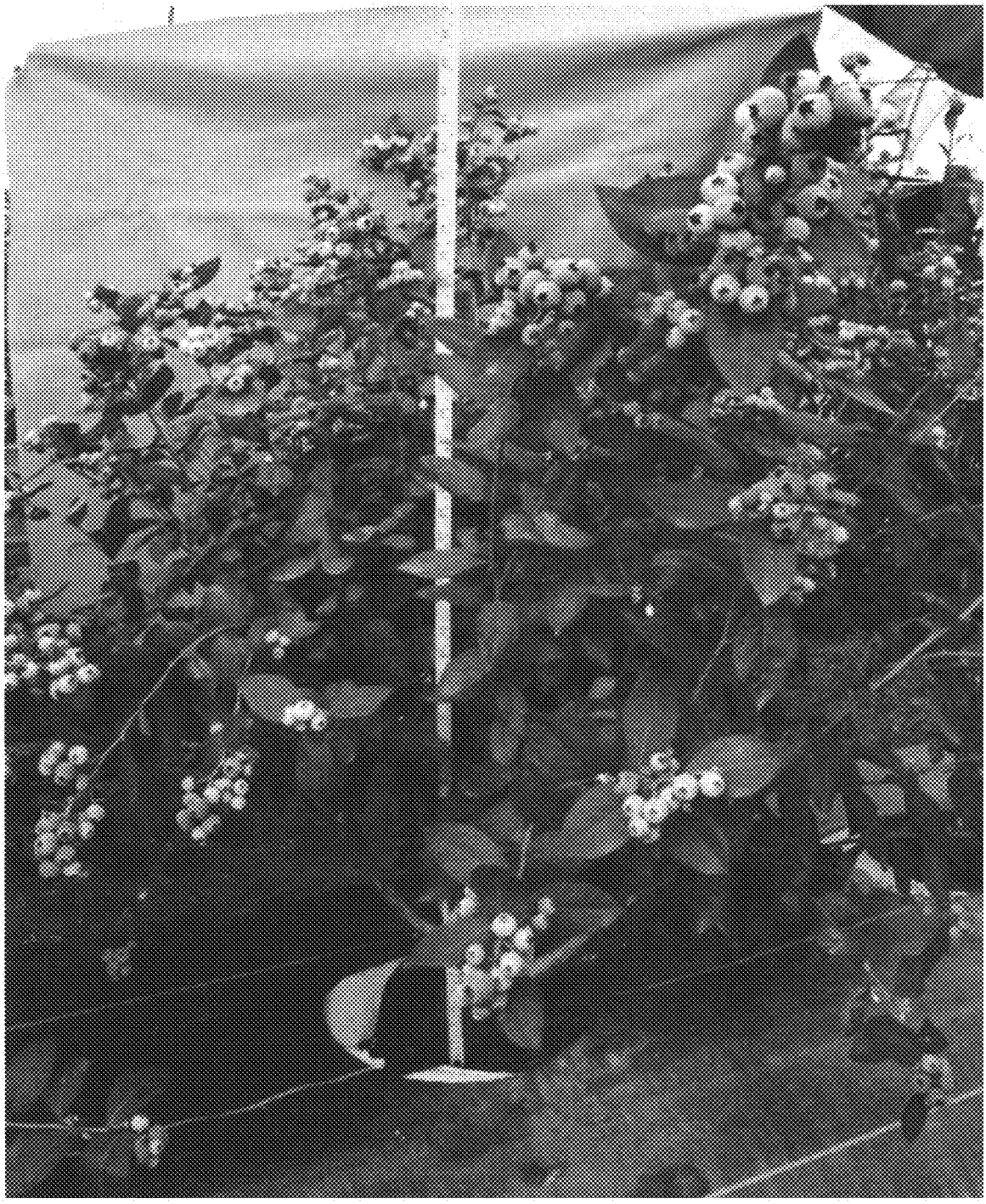
FIG. 8 illustrates another view of a whole plant of variety 'DrisBlueTwentyNine'.

The following description sets forth the distinctive characteristics of 'DrisBlueTwentyNine'. The data which define these characteristics is based on observations taken in Ciudad Guzmán, Jalisco, México from 2015 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyNine' has not been observed under all possible environmental conditions. Unless noted otherwise, the botanical description of 'DrisBlueTwentyNine' was taken from plants that were four years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family.*—Ericaceae.
*Botanical.*—*Vaccinium corymbosum* L.
*Common name.*—Blueberry.
*Variety name.*—'DrisBlueTwentyNine'.

Parentage:

*Female parent.*—Proprietary blueberry plant '196H3' (unpatented).
*Male parent.*—Proprietary blueberry plant '9J301' (unpatented).

Plant:

*Height.*—103 cm.
*Length.*—82 cm.
*Vigor.*—Strong.
*Growth habit.*—Semi-upright.
*Cane renewal.*—6.
*Chilling requirements.*—'DrisBlueTwentyNine' has fruited in Ciudad Guzmán, Jalisco, México with an average of 100 chill hours or less.
*Time of vegetative bud burst.*—Medium.
*One-year-old shoot* (*young canes*).—Length: 97 cm. Diameter at base: 12.7 mm. Diameter at tip: 2.8 mm. Internode length on the upper half: 23.9 mm. Color: RHS 143C (Strong yellow green).
*Five-year-old canes*(*mature canes*).—Length: 116 cm. Diameter at base: 28 mm. Diameter at tip: 2.7 mm. Internode length on the upper half: 25.2 mm. Color: RHS 144B (Strong yellow green). Texture: Smooth.

Leaves:

*Length.*—7.1 cm.
*Width.*—2.2 cm.
*Length/width ratio.*—Small.
*Shape.*—Ovate.
*Shape of leaf apex.*—Acute.
*Shape of leaf base.*—Cuneate.
*Arrangement.*—Alternate.
*Venation pattern.*—Reticulate.
*Vein color.*—RHS 145B (Light yellow green).
*Margin.*—Entire.

*Color on upper side.*—RHS 137A (Moderate olive green).

*Color on lower side.*—RHS 147B (Moderate yellow green).

*Trichomes.*—Absent.

*Glossiness.*—Medium.

*Glaucosity on upper side.*—Absent.

*Petiole.*—Length: 5.66 mm. Diameter: 2.6 mm. Color: RHS 144B (Strong yellow green.

Flowers:

*Inflorescence.*—Length (excluding peduncle): 12.6 mm. Length (including peduncle): ~20 mm. Length of peduncle: 11.03 mm. Diameter of peduncle: 2.3 mm. Color of peduncle: RHS 144D (Light yellow green).

*Flower bud.*—Length: 7.0 mm. Width: 2.9 mm. Number of flowers per bud: 6. Anthocyanin coloration: Weak. Flower bud color: RHS 155A (Pale yellow green).

*Flower pedicel.*—Length: 9.1 mm. Diameter: 0.8 mm. Color: RHS 144B (Strong yellow green).

*Corolla.*—Length: 12.1 mm. Width: 9.1 mm. Diameter of corolla aperture: 4.3 mm. Petal width (ridge to ridge): 8.8 mm. Shape: Urceolate. Size of corolla tube: Medium. Color of corolla tube: RHS 155D (Yellowish white). Anthocyanin coloration of corolla tube on outer side: Absent. Ridges on corolla tube: Present. Conspicuousness of ridges on corolla tube: Strong. Other: Fruit tends to retain the corolla.

*Sepal.*—Length: 5.4 mm. Width: 6,4 mm. Color: RHS 190B (Pale green).

*Reproductive organs.*—Style length: 7 mm. Style color: RHS 145A (Strong yellow green). Ovary color: RHS 190B (Pale green). Stamen length: 5.3 mm. Stamen color: RHS 164A (Brownish orange). Pollen amount: Medium. Pollen color: RHS 1D (Pale greenish yellow).

*Color of receptacle.*—RHS 190B (Pale green).

*Fragrance.*—Absent.

*Flowering interval on one-year-old shoot.*—June to August.

*Flowering interval on current year's shoot.*—July to January.

Fruit:

*Length.*—12.4 mm.

*Width.*—17.5 mm.

*Weight.*—3.3 g.

*Size.*—Large.

*Shape in longitudinal section.*—Oblate.

*Attitude of sepals.*—Erect.

*Type of sepals.*—Straight.

*Calyx basin.*—Diameter: 7.1 mm. Depth: 2.2 mm.

*Infructescence* (*fruit cluster*).—Number of berries per cluster: 5. Peduncle length: 7.5 mm. Peduncle diameter: 2.3 mm. Pedicel length: 12.7 mm. Pedicel diameter: 1.0 mm. Density: Medium.

*Color of unripe fruit.*—RHS 136D (Light yellowish green).

*Intensity of bloom.*—Weak, tending to have a "stripy" bloom.

*Color of skin after removal of bloom on mature fruit.*—RHS 103A (Greyish purplish blue).

*Fruit firmness.*—Firm.

*Sweetness/soluble solids* (*in °Brix*).—12.1.

*Titratable acidity* (*% as citric acid*).—0.5.

*Seed.*—Diameter: 1.7 mm. Color: RHS N167B (Brownish orange). Number: 14 seeds per fruit.

*Fruiting.*—Fruiting type: On one-year-old and current season's shoots. Harvest interval on one-year-old shoot: Mid-August to mid-January. Harvest interval on current year's shoot: Mid-September to mid-February, ~every 15 days. Yield: 2.6 kg to 3.0 kg of fruit per plant per season from 48-month old plants when grown at Ciudad Guzmán, Jalisco, México.

Resistance to abiotic stress, pests, and diseases:

*Drought.*—Susceptible.

*Heat.*—Moderately resistant.

*Blueberry bud mite* (*Acalitus vaccinii*).—Moderately susceptible.

*Spotted-wing drosophila* (*Drosophila suzukii*).—Moderately susceptible.

*Botrytis fruit rot* (*Botrytis cinerea*).—Susceptible.

COMPARISONS TO PARENTAL AND REFERENCE BLUEBERRY VARIETIES

'DrisBlueTwentyNine' differs from the female parent proprietary blueberry plant '196H3' unpatented) in that 'DrisBlueTwentyNine' has firmer fruit, smaller picking scar, and sweeter flavor than '196H3'. In addition, 'DrisBlueTwentyNine' has higher yield potential and matures earlier than '196H3'.

'DrisBlueTwentyNine' differs from the male parent proprietary blueberry plant '9J301' (unpatented) in that 'DrisBlueTwentyNine' has firmer fruit and larger fruit size than '9J301'.

'DrisBlueTwentyNine' differs from the reference blueberry plant variety 'DrisBlueNineteen' (U.S. Plant Pat. No. 31,698) in that 'DrisBlueTwentyNine' has medium time of vegetative bud burst, early time of beginning of flowering on one-year-old shoot, weak intensity of bloom on fruit, and medium time of beginning of fruit ripening on current year's shoot, whereas 'DrisBlueNineteen' has early time of vegetative bud burst, very early time of beginning of flowering on one-year-old shoot, medium intensity of bloom on fruit, and early time of beginning of fruit ripening on current year's shoot.

'DrisBlueTwentyNine' differs from the reference blueberry plant variety 'DrisBlueThirteen' (U.S. Plant Pat. No. 26,451) in that 'DrisBlueTwentyNine' has medium time of vegetative bud burst, weak flower bud anthocyanin coloration, large fruit size, and bears fruit on one-year-old and current season's shoots, whereas 'DrisBlueThirteen' has very early time of vegetative bud burst, very strong flower bud anthocyanin coloration, medium fruit size, and bears fruit on one-year-old shoots only.

What is claimed is:

1. A new and distinct variety of blueberry plant designated 'DrisBlueTwentyNine' as shown and described herein.

* * * * *